US00PP22604P2

(12) United States Plant Patent
Bradford

(10) Patent No.: US PP22,604 P2
(45) Date of Patent: Mar. 27, 2012

(54) PLUM TREE NAMED 'BLACK MAJESTY III'

(50) Latin Name: *Prunus salicina*
Varietal Denomination: Black Majesty III

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/928,676

(22) Filed: Dec. 17, 2010

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP13,476 P2 1/2003 Bradford

*Primary Examiner* — Annette Para

(57) ABSTRACT

The present invention relates to a plum tree and more particularly to a new and distinct variety broadly characterized by a medium size, vigorous, hardy, and productive tree. Being self-unfruitful, the present variety requires cross pollination from a plum that blooms during the early season. The fruit matures under the ecological conditions described during mid July, with first picking on Jul. 9, 2010. The fruit is uniformly medium in size, blackish purple in skin color, clingstone in type, oblate to cordate in shape, brilliant greenish yellow in flesh color, firm in texture, and mildly sweet in flavor.

1 Drawing Sheet

Botanical classification: *Prunus salicina.*
Varietal denomination: 'BLACK MAJESTY III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Black Majesty III'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing a group of five different plum trees was crossed by me in this manner. To pollinate the plum trees in this house, I selected bouquets from several sources of plum and interspecific trees without keeping specific written details. Upon reaching maturity the fruit from these plum trees was harvested and the seeds were removed, cracked, stratified and germinated as a group with the label "H8". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to 'Yummyrosa' (U.S. Plant Pat. No. 13,476) plum by being productive, by being self-unfruitful and by producing fruit that is medium in size, sweet in flavor, mostly oblate in shape, and clingstone in type but is distinguished therefrom by flowering in the early instead of mid season and by producing fruit that is almost entirely yellow in flesh color without red bleeding, that is much less prone to dropping, and that matures about seven days later.

SUMMARY OF VARIETY

The present plum variety is characterized by a medium size, vigorous, hardy, and productive tree. Being self-unfruitful, the present variety requires cross pollination from a plum that blooms during the early season. The fruit matures under the ecological conditions described during mid July, with first picking on Jul. 9, 2010. The fruit is uniformly medium in size, blackish purple in skin color, clingstone in type, oblate to cordate in shape, brilliant greenish yellow in flesh color, firm in texture, and mildly sweet in flavor.

DRAWING

The accompanying photograph consists of four whole fruits positioned to display the characteristics of the skin color and form, two half fruits divided to reveal the flesh and stone, a young tip shoot growth, typical leaves, and three insets depicting the flower buds and blossoms as they appeared on the tree during the blooming season.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jul. 15, 2010, on the original tree during its ninth growing season. The flower and bud descriptions were developed during the previous blooming season. All major color code designations are by reference to the Inter-Society Color Council, National Bureau of Standards. Common color names are also used occasionally.

It is to be noted that the climatic conditions in 2010 led to delayed fruit ripening for most of the season by approximately ten days. This should be taken into account when comparing to other variety descriptions made referencing different years. However, the relative blooming times and ripening times cited in this application are accurate for 2010, and should remain about the same in future years.

Parentage

Seed parent: Unknown.
Pollen parent: Unknown.

Tree

Size: Medium, reaching and maintaining a height of 10' [3.05 m.] and a spread of 8' [2.44 m.] after nine growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable early seasonal blooming plum such as 'Yummygem' (U.S. Plant Pat. No. 15,809).

Bearing: Regular bearing observed thus far, weather dependent.

Trunk:
- *Size*.—Medium, reaching a maximum diameter of 4⅝" [117.5 mm.] after the ninth growing season.
- *Texture*.—Medium shaggy.
- *Bark color*.—A Dark brown [59. d.Br] and Dark grayish brown [62. d.gy.Br] variegation with a few Light yellowish brown [76. 1.yBr] crevices present.
- *Lenticels*.—Approximate Number Per Square Inch: 8. Color: Dark orange yellow [72. d.OY]. Average Size: 5/16" [7.9 mm.]. Shape: Eye-shaped, elongated.

Branches:
- *Size*.—Diameter of the first hanger is 1⅝" [41.3 mm.] measured 12" from the central leader.
- *Texture*.—Smooth on first and second year wood, increasing roughness with age.
- *Color*.—1st Year Wood Topside: Strong yellowish brown [74. s.yBr]. 1st Year Wood Underside: Strong yellow green [117. s.YG]. 2$^{nd}$ Year Wood: Deep brown [56. deep Br] with a Grayish brown [61. gy.Br] variegation. 3$^{rd}$ Year Wood: Dark brown [59. d.Br] with a Dark grayish brown [62. d.gy.Br] variegation.
- *Lenticels*.—Number Per Square Inch: About 80 on second year wood. Color: Dark orange yellow [72. d.OY]. Average Size: 1/16" [1.6 mm.]. Shape: Eye-shaped, elongated.

Leaves:
- *Size*.—Medium. Average Length: 4" [101.6 mm.]. Average Width: 2" [50.8 mm.].
- *Arrangement*.—Alternate.
- *Thickness*.—Medium.
- *Form*.—Elliptical.
- *Apex*.—Acuminate.
- *Base*.—Acute with an average angle base angle of 60 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: ⅜" [9.5 mm.]. Average Thickness: 1/16" [1.6 mm.]. Color: Moderate yellow green [120. YG].
- *Stipules*.—Number: Up to 2 per leaf, up to 6 per growing tip. Average Length: ¼" [6.4 mm.]. Color: Light yellow green [119. 1.YG] becoming Light reddish brown [42. 1.rBr] with age.
- *Glands*.—Number: 1 to 4 per leaf, mostly 2. Position: Alternately positioned at the intersection of the petiole and on the leaf blade. Size: Small. Form: Globose. Color: Light yellow green [119. 1.YG] becoming Grayish reddish brown [46. gy.rBr] in the center with age.
- *Leaf buds*.—Pointed, medium.

Flower buds:
- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.
- *Average flower diameter*.—⅞" [22.2 mm.].
- *Number of petals*.—Five, no double blossoms observed.
- *Petal shape*.—Oval to circular.
- *Petal margin*.—Entire, smooth to slightly wavy.
- *Average petal diameter*.—7/16" [11.1 mm.].
- *Average petal length*.—½" [12.7 mm.].
- *Petal apex*.—Rounded.
- *Petal base*.—Obtuse.
- *Petal color*.—White [263. White] on both sides.
- *Anther color*.—Strong orange yellow [68. s.OY] over a Brilliant yellow [83. brill.Y] center.
- *Stigma color*.—Light greenish yellow [101 1.gY].
- *Sepal color*.—Brilliant yellow green [116. brill.YG] on the outer surface.
- *Sepal length*.—3/16" [4.8 mm.].
- *Sepal width*.—⅛" [3.2 mm.].
- *Sepal apex*.—Rounded to elliptical to match the width and length.
- *Sepal margin*.—Fairly smooth with slight serrations toward the apex.
- *Average pistil length*.—½" [12.7 mm.].
- *Average stamen length*.—⅜" [9.5 mm.].
- *Fragrance*.—Moderate.
- *Bloom density*.—Heavy.
- *Number per cluster*.—2 to 8, average 5.
- *Pollen production*.—Medium, average enticement to bees.
- *Blooming period*.—Early, about three days after 'Yummygem' (U.S. Plant Pat. No. 15,809) plum.
- *Onset of bloom*.—One percent on Feb. 14, 2010.
- *Date of full bloom*.—Feb. 23, 2010.

*Duration of bloom*.—One to two weeks, dependent on ambient temperature.

Fruit

Maturity when described: Firm ripe, Jul. 15, 2010.
Date of first picking: Jul. 9, 2010.
Date of last picking: Jul. 19, 2010.
Size: Uniform, medium.
*Average diameter axially*.—2 5/16" [58.7 mm.].
*Average diameter across cheek plane*.—2 11/16" [68.3 mm.].
*Average diameter across suture plane*.—2 3/4" [69.9 mm.].
*Typical weight*.—4.9 ounces [139 grams].
Form: Uniform, globose, symmetrical.
*Longitudinal section form*.—Oblate to cordate if viewed parallel to the suture.
*Transverse section through axial diameter*.—Round.
Suture: An inconspicuous shallow groove extending from the base to the apex, slightly sharper toward both the base and apex.
Ventral surface: Rounded, slightly lipped toward the apex.
Lips: Usually equal, unequal on a few.
Cavity: Circular, suture showing on one side, stem indentations occur occasionally.
*Depth*.—7/16" [11.1 mm.].
*Breadth*.—3/4" [19.1 mm.].
Base: Cordate and slightly truncate.
Apex: Rounded.
Pistil point: An inconspicuous Light yellowish brown [76. l.yBr] dot located at the end of the suture.
Stem: Medium.
*Average length*.—7/16" [11.1 mm.].
*Average width*.—1/8" [3.2 mm.].
Skin:
*Thickness*.—Medium.
*Surface*.—Smooth.
*Tenacity*.—Tenacious to the flesh.
*Astringency*.—Slightly bitter.
*Tendency to crack*.—None observed in dry season.
*Color*.—Blackish purple [230. bk.P] with a minor amount of Light yellow green [119. l.YG] freckling throughout.
*Bloom*.—Abundant.
Flesh:
*Color*.—Brilliant greenish yellow [98. brill.gY] with some Light orange yellow [70. l.OY] streaking near the stone.
*Surface of pit cavity*.—Covered with Brilliant orange yellow [67. brill.OY] broken fibers when twisted away from the stone.
*Amygdalin*.—Moderate.
*Juice*.—Moderate, rich.
*Texture*.—Firm, meaty.
*Fibers*.—Few, fine, tender.
*Ripens*.—Fairly evenly, slightly earlier toward the apex.
*Flavor*.—Mild, sweet with moderate acid, typically 15 to 17 brix.
*Aroma*.—Very slight.
*Eating quality*.—Very good.

Stone

Type: Clingstone.
Form: Oval.
Hilum: Narrow.
Base: Straight, slightly cordate.
Apex: Acuminate with a sharp 1/16" [1.6 mm.] tip.
Sides: Equal.
Surface: Rough throughout with a groove on each side of the dorsal fin.
External color of stone: Light olive brown [94. l.olBr] when dry.
Pit wall color when cracked: Light brown [57. l.Br].
Cavity surface color: Light grayish yellowish brown [79. l.gy.yBr].
Average pit wall thickness: 1/8" [3.2 mm.]
Average width: 11/16" [17.5 mm.].
Average length: 7/8" [22.2 mm.].
Average breadth: 3/8" [9.5 mm.].
Tendency to split: None.
Kernel:
*Form*.—Oval.
*Skin color*.—Light greenish yellow [101. l.gY].
*Pellicle color*.—Very greenish yellow [97. v.gY].
*Vein color*.—Brilliant greenish yellow [98. brill.gY].
*Taste*.—Slightly bitter.
*Viable*.—Yes.
*Average width*.—7/16" [11.1 mm.].
*Average length*.—9/16" [14.3 mm.].
*Amygdalin*.—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is similar to 'Yummyrosa' (U.S. Plant Pat. No. 13,476) plum by being productive, by being self-unfruitful, and by producing fruit that is medium in size, sweet in flavor, mostly oblate in shape, and clingstone in type but is distinguished therefrom by flowering in the early instead of mid season and by producing fruit that is almost entirely yellow in flesh color without red bleeding, that is much less prone to dropping, and that matures about seven days later.

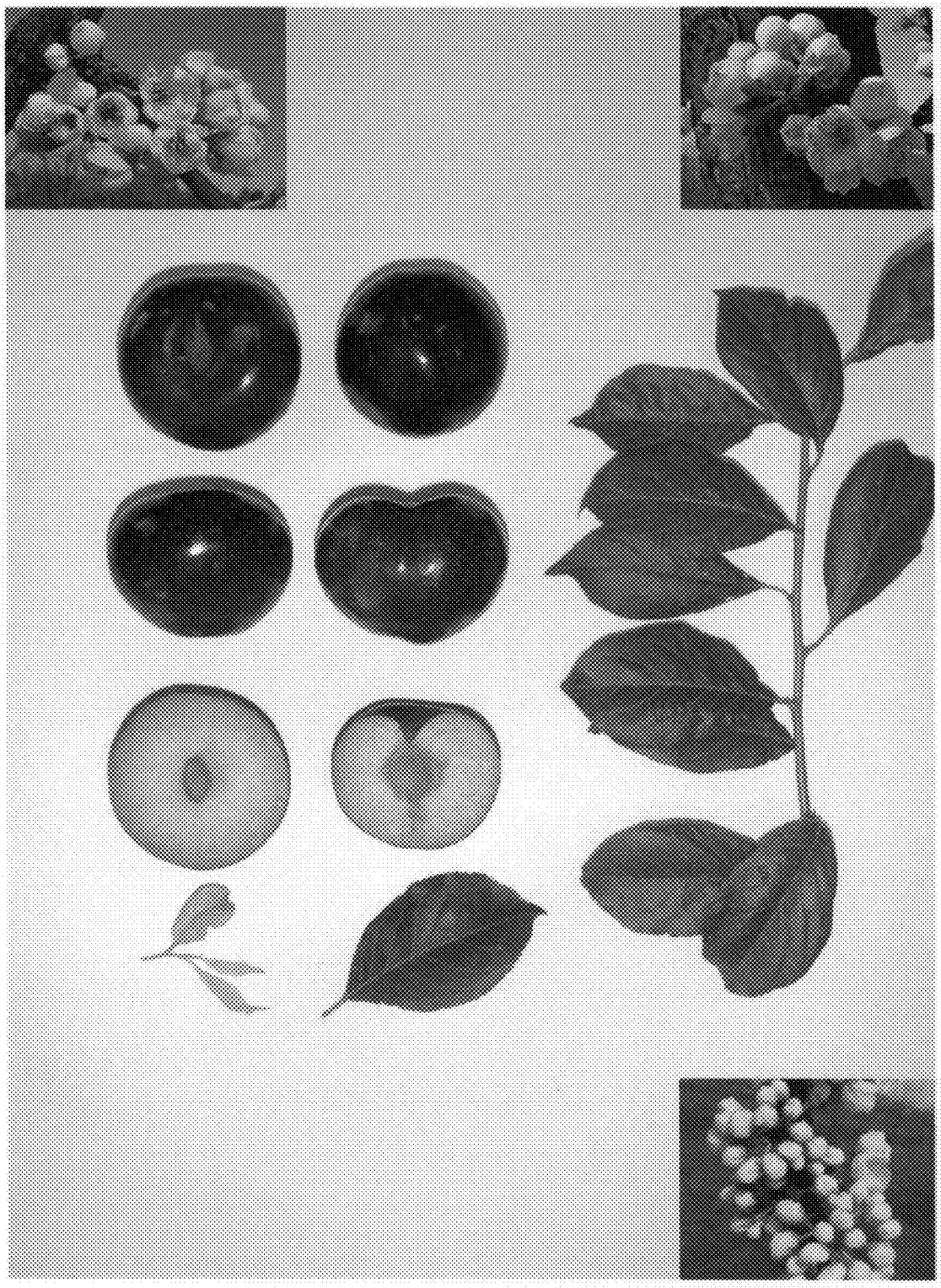

* * * * *